(12) United States Patent
Early

(10) Patent No.: US 10,617,790 B2
(45) Date of Patent: Apr. 14, 2020

(54) DECELLULARIZED BIOMATERIAL FROM NON-MAMMALIAN TISSUE

(71) Applicant: ISE Professional Testing & Consulting Services, Inc., Eustis, FL (US)

(72) Inventor: Ryanne Early, Fleming Island, FL (US)

(73) Assignee: ISE Professional Testing & Consulting Services, Inc., Fleming Island, FL (US)

( * ) Notice: Subject to any disclaimer, the term of this patent is extended or adjusted under 35 U.S.C. 154(b) by 0 days.

(21) Appl. No.: 14/759,895

(22) PCT Filed: Jan. 9, 2014

(86) PCT No.: PCT/US2014/010890
§ 371 (c)(1),
(2) Date: Jul. 8, 2015

(87) PCT Pub. No.: WO2014/110269
PCT Pub. Date: Jul. 17, 2014

(65) Prior Publication Data
US 2015/0352257 A1 Dec. 10, 2015

Related U.S. Application Data

(60) Provisional application No. 61/750,555, filed on Jan. 9, 2013.

(51) Int. Cl.

| | |
|---|---|
| *A61L 27/36* | (2006.01) |
| *A61K 9/70* | (2006.01) |
| *A61L 27/58* | (2006.01) |
| *A61K 35/12* | (2015.01) |
| *C12N 5/071* | (2010.01) |
| *A61L 27/60* | (2006.01) |
| *A61L 27/54* | (2006.01) |
| *A61K 38/17* | (2006.01) |

(Continued)

(52) U.S. Cl.
CPC ............ *A61L 27/3687* (2013.01); *A61K 9/70* (2013.01); *A61K 35/12* (2013.01); *A61K 35/65* (2013.01); *A61K 38/1703* (2013.01); *A61L 27/362* (2013.01); *A61L 27/3604* (2013.01); *A61L 27/3625* (2013.01); *A61L 27/3633* (2013.01); *A61L 27/3691* (2013.01); *A61L 27/38* (2013.01); *A61L 27/52* (2013.01); *A61L 27/54* (2013.01); *A61L 27/58* (2013.01); *A61L 27/60* (2013.01); *C12N 5/0625* (2013.01); *A61L 2300/252* (2013.01); *A61L 2300/412* (2013.01); *A61L 2300/604* (2013.01); *A61L 2300/606* (2013.01); *A61L 2300/64* (2013.01); *A61L 2430/34* (2013.01); *A61L 2430/40* (2013.01); *C12N 2533/90* (2013.01); *C12N 2533/92* (2013.01)

(58) Field of Classification Search
CPC .......... A61K 35/65; A61K 35/12; A61K 9/70; A61L 37/3687; A61L 37/58; A61L 37/60; A61L 37/54; A61L 37/362; C12N 5/0625
See application file for complete search history.

(56) References Cited

U.S. PATENT DOCUMENTS

| 4,298,002 A | 11/1981 | Ronel et al. |
|---|---|---|
| 4,361,552 A | 11/1982 | Baur |

(Continued)

FOREIGN PATENT DOCUMENTS

| CN | 1791331 A | 6/2006 |
|---|---|---|
| CN | 1969039 A | 5/2007 |

(Continued)

OTHER PUBLICATIONS

Smith et al., "Collagens From the Skin and Cartilage of the Larval Salamander Ambystoma tigrinum", J of Exp Zoology, 220:243-250, 1982.*

(Continued)

*Primary Examiner* — Ruth A Davis
(74) *Attorney, Agent, or Firm* — DLA Piper LLP (US)

(57) ABSTRACT

The growth factor profile, connective tissue matrix constituents, and immunoprivileged status of urodele extracellular matrix (ECM) and accompanying cutaneous tissue, plus the presence of antimicrobial peptides there, render urodele-derived tissue an ideal source for biological scaffolds for xenotransplantation. In particular, a biological scaffold biomaterial can be obtained by a process that entails (A) obtaining a tissue sample from a urodele, where the tissue comprises ECM, inclusive of the basement membrane, and (B) subjecting the tissue sample to a decellularization process that maintains the structural and functional integrity of the extracellular matrix, by virtue of retaining its fibrous and non-fibrous proteins, glycoaminoglycans (GAGs) and proteoglycans, while removing sufficient cellular components of the sample to reduce or eliminate antigenicity and immunogenicity for xenograft purposes. The resultant urodele-derived biomaterial can be used to enhance restoration of skin homeostasis, to reduce the severity, duration and associated damage caused by post-surgical inflammation, and to promote progression of natural healing and regeneration processes. In addition, the biomaterial promotes the formation of remodeled tissue that is comparable in quality, function, and compliance to undamaged human tissue.

36 Claims, 6 Drawing Sheets

(51) Int. Cl.
*A61L 27/38* (2006.01)
*A61K 35/65* (2015.01)
*A61L 27/52* (2006.01)

(56) References Cited

U.S. PATENT DOCUMENTS

| | | | |
|---|---|---|---|
| 6,485,969 B1 * | 11/2002 | Asem | C12N 5/0068 435/1.1 |
| 2004/0181240 A1 | 9/2004 | Tseng et al. | |
| 2006/0153797 A1 | 7/2006 | Bortolotto et al. | |
| 2008/0046095 A1 | 2/2008 | Daniel | |
| 2010/0104539 A1 | 4/2010 | Daniel et al. | |

FOREIGN PATENT DOCUMENTS

| | | |
|---|---|---|
| CN | 101337089 A | 1/2009 |
| CN | 102227225 A | 10/2011 |
| JP | 2004-521935 A | 4/2004 |
| JP | 2007-532153 A | 11/2007 |
| JP | 2009-510091 A | 3/2009 |
| JP | 2009-513269 A | 4/2009 |
| WO | 02/078720 A2 | 10/2002 |
| WO | WO 03/082201 A2 | 10/2003 |
| WO | WO 2005/009498 A2 | 2/2005 |
| WO | 2005/097219 A1 | 10/2005 |
| WO | 2007/038686 A2 | 4/2007 |
| WO | WO 2007/124127 A2 | 11/2007 |
| WO | WO 2008/129997 A1 | 10/2010 |
| WO | WO 2012/131104 | 10/2012 |
| WO | WO 2012/131106 | 10/2012 |

OTHER PUBLICATIONS

Satoh et al., "Collagen Reconstitution Is Inversely Correlated with Induction of Linb Regeneration in Ambystoma mexicanum", Zoological Science, 29: 191-197, 2012.*
Seifert et al., "Skin Regeneration in Adult Axolotls: A Blueprint for Scar-Free Healing in Vertebrates", PLoS One, www.plosone.org, Apr. 2012, vol. 7, Issue 4, e32875.*
Extended European Search Report for European Application No. 14737892.1 dated Sep. 28, 2016.
International Search Report and Written Opinion for International Application No. PCT/US2014/010890 dated May 15, 2014.
International Preliminary Report on Patentability for International Application No. PCT/US2014/010890 dated Jul. 23, 2015.
Cima et al., Hepatocyte culture on biodegradable polymeric substrates. Biotechnol Bioeng. Jun. 20, 1991;38(2):145-58.
Meller et al., Amniotic Membrane Transplantation in the Human Eye. Deutsches Arzteblatt International. Apr. 2011;108(14):243-248.
Tottey et al., The effect of source animal age upon extracellular matrix scaffold properties. Biomaterials. Jan. 2011; 32(1):128-36.
Vacanti et al., Selective cell transplantation using bioabsorbable artificial polymers as matrices. J Pediatr Surg. Jan. 1988;23(1 Pt 2):3-9.
Vacanti et al., Synthetic polymers seeded with chondrocytes provide a template for new cartilage formation. Plast Reconstr Surg. Nov. 1991;88(5):753-9.
Wiens et al., Ontogeny discombobulates phylogeny: paedomorphosis and higher-level salamander relationships. Systematic Biology. Feb. 2005; 54(1): 91-110.
Zaiou, Multifunctional antimicrobial peptides: therapeutic targets in several human diseases. Journal of Molecular Medicine. Apr. 2007; 85(4):317-29, Epub Jan. 10, 2007.
Satoh et al., Collagen reconstitution is inversely correlated with induction of limb regeneration in Ambystoma mexicanum. Zoolog Sci. Mar. 2012;29(3):191-7. doi: 10.2108/zsj.29.191.
Duan et al., Preliminary study on porous scaffold prepared with decellularized artery. Zhongguo Xiu Fu Chong Jian Wai Ke Za Zhi. Sep. 2010;24(9):1052-7, Y—Abstract Only.
Meng et al., An experimental study of extracellular matrix of conjunctiva. Journal of Injusries and Occupational Diseases of the Eye with Ophthalmic Surgeries. May 2007;1:26-8, Y—Abstract Only.
Umashankar et al., Glutaraldehyde Treatment Elicits Toxic Response Compared to Decellularization in Bovine Pericardium. Toxicol Int 2012;19(1):51-8.
Second Office Action from counterpart Chinese Patent Appln. No. 201480013359.0 dated May 22, 2019, along with its English Translation.
Notice for Reasons of Refusal from counterpart Japanese Patent Appln. No. 2018-224475 dated Feb. 3, 2020, and its English translation.

* cited by examiner

| Epoch Plate Reader | Avg. Duplicate | | | |
|---|---|---|---|---|
| Sample ID | 260/280 | dsDNA conc. ng/ul | dsDNA conc. ug/ul | Percent Reduction |
| A-Native | 2 | 1702.8 | 1.7028 | 89.8% |
| A-Native | 2 | 1977.5 | 1.9775 | 92.8% |
| A-Native | 2 | 1618.3 | 1.6183 | 92.7% |
| A-P1 | 1.96 | 173.7 | 0.1737 | |
| A-P2 | 1.95 | 141.7 | 0.1417 | |
| A-P3 | 1.97 | 117.9 | 0.1179 | |
| BioDlogic (BioD) | 2 | 1.34 | 0.00134 | |
| Biotissue (Amniograft) | 1.5 | 27.81 | 0.02781 | |
| Mimedx (Amniofix) | 1.26 | 104.6 | 0.1046 | |
| Seed Biotech (Aril) | 1.75 | 3.16 | 0.00316 | |

Paired native and post decellurization urodele connective tissue Residual DNA Analysis Commercially available Amniotic Membrane Products residual Dna

FIGURE 6

DECELLULARIZED BIOMATERIAL FROM NON-MAMMALIAN TISSUE

CROSS-REFERENCE TO RELATED APPLICATIONS

This application is a national stage filing under 35 U.S.C. § 371 of PCT International application PCT/US2014/010890 designating the United States of America, filed Jan. 9, 2014 which claims the benefit under 35 USC § 119(e) to U.S. provisional application 61/750,555, filed Jan. 9, 2013, the entire contents of which are incorporated herein by reference in their entirety.

BACKGROUND OF THE INVENTION

Tissue engineering efforts are ongoing to produce methods and materials for replacing biological functions, typically repairing or replacing whole tissues or portions thereof. In this regard, wound treatment and skin repair are areas of predominant focus, as the loss of skin integrity due to illness or injury can lead to chronic, life threatening complications.

Wound healing involves complex interactions between cells, growth factors, and extracellular matrix (ECM) components to reconstitute tissue following injury. The wound healing process in adult mammalian tissue has been well characterized and can be broken down into three stages—inflammation, proliferation, and remodeling.

Typically, in response to an incision or trauma the body conveys blood, blood products, and proteins into the void (also referred to as the cavity or negative space) formed at the wound. During early inflammation, a wound exudate begins to form under the influence of inflammatory mediators and as a result of vasodilation. Fibrin and fibronectin present in clotting blood provide a scaffold over which cells such as keratinocytes, platelets and leukocytes migrate to the wound site. Bacteria and debris are phagocytosed and removed, and growth factors are released that stimulate the migration and division of fibroblasts.

The subsequent stage of wound healing involves new tissue formation as fibrous connective tissue, termed granulation tissue (composed of fibroblasts, macrophages and neovasculature) replaces the fibrin clot. New blood vessels are formed during this stage, and fibroblasts proliferate and produce a provisional ECM by excreting collagen and fibronectin. Nearly all mammalian cells require adhesion to a surface in order to proliferate and function properly. The ECM fulfills this function. Initially, the provisional ECM contains of a network of Type III collagen, a weaker form of collagen that is rapidly produced. This is later replaced by the stronger Type I collagen (which contributes to scar formation). At the same time, re-epithelialization of the epidermis occurs. During this process, epithelial cells proliferate and migrate over the newly forming tissue as proteases such as metalloportineaes (MMPs) and collagenases at the leading edge of the migrating cells help to invade the clot. These enzymes in addition to growth factor signaling (cell-cell interactions) and cell-ECM interactions (signal transduction from interactions between cells, integrins (cell surface receptors), laminin, collagen, fibronectin, and other ECM proteins) stimulate cell migration into the wound and ECM degradation.

Finally, in the remodeling phase, collagen is remodeled and realigned along tension lines and cells that are no longer needed are removed by apoptosis. Wound contraction occurs as fibroblasts transform into myofibroblasts through their interactions with ECM proteins and growth factors. Myofibroblasts then interact with collagen, vitronectin, and other ECM proteins to contract the wound. As the remodeling phase proceeds, fibronectin and hyaluronic acid are replaced by collagen bundles that lend strength to the tissue.

By applying biological, chemical and engineering principles to tissue repair and regeneration, tissue engineers have developed transplantable products for use in promoting the tissue repair and regeneration processes. The ability to restore biomechanical function of damaged tissue presents a true challenge. In response, both synthetic and biological scaffold products have been developed that mimic (to some extent) tissue structure and mechanical behavior to promote tissue repair. Such products serve as a temporary replacement, both mechanically and functionally, for damaged, diseased or absent tissue.

Ideally, transplantable scaffold products should support cell adhesion, proliferation and differentiation and act as an interim synthetic extracellular matrix (ECM) for cells prior to the formation of new tissue. Scaffold materials should be biocompatible, biodegradable and exhibit low antigenicity. The implant should degrade at a rate roughly equal to that of the new tissue formation. Once implanted, the scaffold must have the mechanical properties necessary to temporarily offer structural support until the new tissue has formed. Additionally, scaffold products must be porous, providing an appropriate path for nutrient transmission and tissue ingrowth. Tissue scaffolds also should promote fast healing and facilitate the development or regeneration of new tissue that resembles normal host tissue in both appearance and function. To this end, implanted scaffold products should offer (i) bioactive stimulation, e.g., protein and molecular signaling, to encourage cell migration, proliferation and differentiation, and (ii) mechanical or structural support for these processes.

Today, the development of synthetic scaffolds is an area of active research. Synthetic scaffolds have been manufactured from chemical compounds such as fibrous polymers, gelatin, apatite, and polymer/ceramic composites, polylactic acid, collagen. These scaffolds are designed to mimic the structure of the naturally occurring ECM and have shown some success in bone tissue engineering.

In addition to synthetic scaffold products, biological scaffolds obtained from mammalian tissues are commercially available for use as allografts (transplanted cell or tissue from a donor of the same species) or xenografts (transplanted cells or tissue from a donor of a different species). Biological scaffolds are composed of mammalian ECM harvested from, for example, dermis, urinary bladder, small intestine, mesothelium, pericardium, bone or aminiotic membrane of various mammals including human (either live donor or cadaver), porcine, bovine and equine. These commercially available products are commonly used for the repair and reconstruction of injured or missing tissues and organs such as soft tissue, tendons, cardiac tissue, neural tissue, chronic wounds, dura mater, bone and cornea.

Biological scaffold products may comprise skin cells in addition to extracellular matrices produced by tissue and subjected to a decellularization process. They are contacted with a wound site to give mechanical support for cell migration and proliferation as part of the wound healing process. In addition, factors such as growth factors or other proteins also may be provided that promote the wound healing process. The mechanical and material properties of biological scaffolds and the host tissue response to these biomaterials are believed to be influenced by the three dimensional configuration of the material and production processing methods. It further is believed that growth factors, surface topology and the distribution of surface ligands and modulation of the host innate immune response all contribute to the eventual functional performance of biological scaffolds for tissue repair or reconstruction. Tottey et al., *Biomaterials* 32: 128-36 (2011).

In transplantation the use of human amniotic membrane (AM) has particular advantages, due to the structure of the relatively thick basement membrane, associated devitalized amniotic epithelial cells and stroma, and corresponding growth factor profile and structural protein composition. Meller et al., *Dtsch Arztebl Int'l* 108: 243-8 (2011). For example, AM contains epidermal growth factor (EGF) and keratinocyte growth factor (KGF), which are important growth factors for promoting wound healing. In addition, laminin and type VII collagen present in the AM elicit an epitheliotropic effect. AM also is thought to reduce the expression of various growth factors and pro-inflammatory cytokines while releasing anti-inflammatory cytokines such as IL-10, IL-1 receptor antagonists, thus modulating the inflammatory response favorably for wound healing. AM is immunoprivileged, moreover, likely by virtue of low MHC I expression, and so rejection of AM tissue is uncommon. These characteristics make AM an ideal substrate, for instance, with respect to ocular surface reconstruction, in pelvic reconstruction, and in the treatment of ulcers, among other wound-healing applications.

The use of conventional tissue scaffold products is not without drawbacks, however. Tissue harvesting from human donors can produce undesirable consequences such as donor site morbidity or infection associated with removal of skin for donation. Disease transmission risk and intersample variation are additional drawbacks associated with biological scaffold products. In addition, it may be difficult to obtain sufficient tissue components necessary to cover large areas of damaged tissue. Furthermore, conventional biological and synthetic materials can be costly, not effective in many instances, and limited in availability.

Accordingly, an abiding exists need for suitable tissue substrate biomaterial for use in transplantation to promote tissue regeneration while restoring functionality. Both the research industry and the medical transplant community would benefit from such a product that is readily available, does not impose additional complications to a donor or recipient (such as requiring an additional surgery to harvest the substrate), and exhibits all or some of the inherent material functionality reflective of the physiochemical, electrochemical, and biochemical properties of natural tissue.

SUMMARY OF THE INVENTION

The biomaterial of the present invention is obtained from tissue of a urodele. "Urodele" here denotes a salamander of the order Urodela, also known as the order Caudata, in the class Amphibia. In terms of phylogeny the relevant families include Ambystomatidae, Cryptobranchidae, Amphiumidae, Proteidae, and Sirenidae. See Wiens et al., *Syst. Biol.* 54: 91-110 (2005), the contents of which are incorporated here by reference in their entirety. Accordingly, the urodele category includes, for example, the Pacific Giant Salamander (*Andrias davidianus*), the Tiger Salamander (*Ambystoma tigrinum*), and the Mexican Axolotl (*Ambystoma mexicanum*). The present inventor has recognized that the skin and ECM of urodeles possess desirable characteristics analogous to those of AM, making them an ideal source of biomaterial for xenotransplantation.

Urodele ECM and Tissue Regeneration

As amphibians, most urodeles begin life as aquatic animals in a larval state and undergo metamorphosis from a juvenile form with gills to an adult, terrestrial, air-breathing form with lungs. During metamorphosis, a urodele's physical features are altered in preparation for life on land. These alterations include caudal fin resorbtion, thickening of the skin, the development of dermal glands and resorption of gills. Sexual maturity also occurs during this time in most urodeles. Some families of urodeles are "neotenic," which means that individuals with such families can exhibit juvenile features, such as gills and fins, even after reaching sexually maturity. Indeed, neotenic urodeles often retain their aquatic (juvenile) form for the duration of their lives. Thus, the Mexican Axolotl normally remains in the neotenic state throughout its adult life although, under certain circumstances, it can undergo metamorphosis and transform into a terrestrial form.

Axolotls also are known for their ability to regenerate amputated body parts, which typically results in the complete restoration of both the structure and function of the damaged limb or organ. Aquatic axolotls undergo rapid re-epithelialization during wound healing and limb regeneration, both of which are scar-less processes. Similarly, metamorphic terrestrial axolotls retain several larval skin features and also exhibit scar-free wound healing, albeit at a slower rate than their aquatic, pre-metamorphic counterpart.

The healing process in axolotls varies from that observed in adult mammals. The axolotl process more closely resembles the scar-free healing process of fetal and embryonic wounds. Thus, such wounds likewise exhibit re-epithelialization and basement membrane reformation that occur at a faster rate (is "enhanced") than do the corresponding events in postnatal mammals.

Moreover, the cutaneous and subcutaneous structures of an axolotl resemble that of the amniotic/chorionic interface, in the sense that axolotl skin is composed of fused ectoderm and mesoderm. Axolotl skin also is rich in growth factors and antimicrobial peptides, similar to the AM. Furthermore, axolotl ECM is immunoprivileged and contains collagen III and tissue inhibitors of metalloproteinases (TIMPs), inter alia, also in resemblance to AM.

Of particular importance for transplantation purposes, more generally, is the immunologically privileged state of the human neonate (e.g., fetal dermis) and the AM, a state mirrored by axolotl ECM, whereby immogenicity is rarely manifested. By virtue of the reduced immune response and the generally decreased inflammatory response as compared to adult humans, neonatal and axolotl skin healing alike are not characterized by accelerated tissue resorption, as is observed in adult human wound healing. Rather, the growth factor profile, enzymatic activity, structural composition and immunomodulating effect of urodele and neonate tissues alike favor an appropriately staged removal of structural scaffolding and tissue growth into the resulting negative void space, in addition to enhanced re-epithelialization, during wound healing. This results in an optimal wound healing environment and process. Also, the high concentration of antimicrobial peptides present in AM and urodele tissue further contributes to the favorable environment and enhanced re-epithelialization observed during wound healing.

A key aspect of the present invention is the inventor's recognition that the growth factor profile, connective tissue matrix constituents, and immunoprivileged status of urodele ECM and accompanying cutaneous tissue, plus the presence of antimicrobial peptides therein, render urodele-derived tissue an ideal source for biological scaffolds for xenotransplantation.

In accordance with the invention, therefore, a biological scaffold biomaterial is provided that is the product of a process comprising (A) obtaining a tissue sample from a urodele, where the tissue comprises ECM, inclusive of the basement membrane, and (B) subjecting the tissue sample to a decellularization process that maintains the structural and functional integrity of the extracellular matrix, by virtue of retaining its fibrous and non-fibrous proteins, glycoaminoglycans (GAGs) and proteoglycans, while removing sufficient cellular components of the sample to reduce or eliminate antigenicity and immunogenicity for xenograft purposes. Also provided is methodology for using the urodele-derived biomaterial to enhance restoration of skin homeostasis, to reduce the severity, duration and associated damage caused by post-surgical inflammation, and to promote progression of natural healing and regeneration processes. In addition, biomaterial of the invention promotes the formation of remodeled tissue that is comparable in quality, function and compliance to undamaged human tissue.

Decellularization

The biomaterial of the invention is produced by decellularizing a tissue sample obtained from a urodele. The primary constituent of the resulting urodele biomaterial is ECM, possibly with devitalized epithelial cells, which can retain moisture and otherwise protect the wound-healing environment.

Urodele skin is one example of an appropriate starting material for the present invention. Thus, the starting material that is subjected to decellularization can comprise urodele dermis and basement membrane, with or without epidermis. Even upon decellularization, moreover, the biomaterial of the invention can comprise, with the ECM, adjacent epithelial cells that may be rendered non-viable by the process. Alternatively, non-cutaneous urodele tissues can serve as the starting material of the invention, particularly those comprising a basement membrane or epithelial tissues that form the lining of various body cavities, i.e., parietal mesothelial tissues found, for example in the thoracic cavity, the abdominal cavity, and pericardium. Tissues that contain substantial amounts of fibrous connective tissue, such as cartilage, tendon, bone, dura mater and fascia, also are illustrative of appropriate starting materials of the present invention.

Effected via any conventional decellularization methodology, urodele tissue decellularization is performed to remove immunogenic cellular antigens that can induce an inflammatory response or immune-mediated tissue rejection, while preserving the structural integrity and composition of the associated ECM. Generally, ECM structural components, many if not all of which remain intact following decellularization, are well-tolerated by xenogeneic recipients. ECM components that may be present in the final biomaterial of the invention include proteins such as collagen (e.g., fibrous collagen I and collagen III, as well non-fibrous collagen IV, collagen V and collagen VII), elastin, fibronectin, laminin, vitronectin, thrombosponsdins, osteopontin and tenascins, plus GAGs (e.g., the proteoglycans, decoran and versican and sulfated GAGs, e.g., heparin sulfate, keratan sulfate, dermatan sulfate and chondroitin sulfate) and growth factors such VEGF, BMP, TGF and FGF. For some indications the post-decellularization material comprises at least collagen IV, laminin, sulfated GAGs and one or more growth factors in amounts that approximate pre-decellularization levels when viewed via histological and immunohistological staining.

Suitable techniques for decellularizing tissues, pursuant to the invention, include physical methods such as freezing, direct pressure application, sonication, and agitation. In addition or in the alternative, chemical methods can be employed, such as alkaline and acid treatments, application of detergents (including amphoteric, cationic, anionic and non-ionic detergents), organic solvents, hypotonic or hypertonic solutions and chelating agents. Enzymatic approaches including protease digestion and treatment with one or more nucleases also may be used to decellularize urodele tissue. In addition or alternatively, the urodele tissue is subjected to cleaning, sterilization, disinfection, antibiotic treatment and/or viral inactivation.

According to one aspect of the invention, a biomaterial is provided. The material is produced by the process that includes (A) obtaining a tissue sample from a urodele, which tissue sample comprises extracellular matrix, and (B) decellularizing the sample to retain structural and functional integrity while removing sufficient cellular components of the sample to reduce or eliminate antigenicity of the biomaterial as a xenograft. In some embodiments, decellularizing comprises subjecting said tissue sample to an alkaline treatment. In embodiments, the process can further comprise subjecting said sample to sterilization. In embodiments, the process can further comprise devitalizing cells.

According to one aspect of the invention, a tissue graft is provided. The graft includes extracellular matrix components derived from a urodele. In embodiments, the extracellular matrix components are substantially free of components that induce an immune response when implanted as a xenograft. In embodiments, the extracellular matrix components are non-toxic.

According to one aspect of the invention, a decellularized Urodele ECM is provided. In any of the embodiments, the decellularized ECM can be derived from Axolotl tissue. In any of the embodiments, the decellularized ECM can include basement membrane. In any of the embodiments, the decellularized ECM can be infused with, coated with, combined with or attached, covalently or non-coalently, to an agent xenogenic to a Urodele. In any of the embodiments, the agent can be any one or any combination of a growth factor, a cytokine, a chemokine, a protein, a carbohydrate, a sugar, a steroid, an antimicrobial agent, a synthetic polymer, an adhesive, a drug and/or a human agent (i.e., an agent found in a human, isolated, synthetically or recombinantly produced). Further such agents forming part of the invention are described in more detail below. In some embodiments, the agent is a cell, optionally a human cell. In some embodiments, the agent is a progenitor cell, optionally a human progenitor cell. Further such cells forming part of the invention are described in more detail below. In any of the embodiments, the decellularized ECM can take on any variety of shapes, as the material can be formed, laminated, homogenized, gelled, etc. In some embodiments, the ECM is a sheet. The sheet optionally can include perforations. The sheet optionally can include a backing and/or an adhesive. The backing may be biodegradable or may be non-biodegradable. In some embodiments, the decellularized ECM is a dry powder. In some embodiments the decelularized ECM is a reconstituted gel. In any of the embodiments, the ECM can be sterile.

According to one aspect of the invention, a package is provided. The package contains sterile, decellularized Urodele ECM or a Urodele fraction derived from the sterile, decellularized Urodele ECM. The package can contain any of the ECMs described above. For example, the package can include a sheet, a dry powder or a reconstituted gel of decellularized Urodele ECM. The package can contain any product, for example any implant, that comprises sterile, decellularized Urodele ECM or a Urodele fraction derived from the sterile, decellularized Urodele ECM. Such an implant may be made in whole or only in minor part of the ECM of the invention.

The invention also provides a sterile medical implant comprising decellularized Urodele ECM or a Urodele fraction derived from the decellularized Urodele ECM. Examples of such medical implants include a biocompatible sheet, mesh, gel, graft, plug, tissue or device. Devices include, for example, coated stents, bone replacements, joint replacements, implantable hardware and the like. The implant can be fabricated entirely or in part from the ECM. The implant also can encapsulate, can be infused with, coated with, impregnated with, laminated with, or covalently or non-covalently attached to the ECM of the invention.

The invention also provides a material, the material being coated with, impregnated with, encapsulating, or having attached thereto isolated, decellularized Urodele ECM or a Urodele fraction derived from the isolated, decellularized Urodele ECM. The material can be natural or synthetic. Examples are metals, plastics, ceramics and fibers.

According to one aspect of the invention, a tissue culture system is provided. The system comprises (a) an isolated Urodele decellularized ECM, (b) tissue culture medium, and (c) cells xenogenic to the Urodele. The cells may be from animal, and in some embodiments, the cell is a mammalian cell. The cell can be any type of cell capable of culture. In embodiments, the cell is a human cell, optionally a progenitor cell.

According to one aspect of the invention, a conditioned tissue culture medium is provided. The medium, which can be any commonly used in liquid tissue culture, is conditioned with isolated Urodele decellularized ECM or a Urodele fraction derived from isolated, decellularized Urodele ECM. Numerous liquid tissue culture media are commercially available and well known to those of ordinary skill in the art.

According to one aspect of the invention, a device is provided. The device is at least two sheets of isolated Urodele decellularized ECM laminated to one another. The sheets can be from the same or different tissue. The sheets can an orientation and can be oriented in the same direction or oriented at angles to one another. The sheets can further comprise any agent xenogenic to the Urodele, which agent may be coated on, infused or impregnated within, or otherwise attached to one or more of the laminated sheets.

In any embodiment described above involving a sheet, the sheet may further comprise a backing and/or adhesive.

According to one aspect of the invention, a product is provided. The product is prepared by isolating Urodele ECM from a Urodele, decellularizing the ECM, and sterilizing the decellularized ECM. The preparation of the device can further involve any one or more of the following steps (presented in no particular order): forming the ECM into a shape, homogenizing the ECM, laminating the ECM to a material, combining agents with the ECM such as by coating, impregnating, or otherwise attaching the agent to the ECM, and so on.

According to one aspect of the invention, a method of preparing a biologic material is provided. The method involves (A) obtaining a tissue sample from a urodele, which tissue sample comprises extracellular matrix, and (B) decellularizing the sample to remove sufficient cellular components of the sample to reduce or eliminate antigenicity of the biomaterial as a xenograft. In embodiments, the method can further involve performing the decellularization in a manner to retain structural and functional integrity of the ECM sufficient to permit the ECM to be useful as a matrix upon and within which cells can grow. In any of the embodiments, the method can further involve homogenizing the ECM to form a particulate or powder. In some embodiments, the method can further involve reconstituting the powder as a gel. In any of the embodiments, the method can further involve sterilizing the ECM. In any of the embodiments, the method can further involve attaching the ECM to an agent xenogenic to a Urodele.

According to another aspect of the invention, the materials such as implants, devices, sheets, gels and powders can be used in methods for treating subjects, where the materials are applied to wounds, surgical beds, and to internal and external tissues, generally, to prevent adhesion, provide tissue support, for example for suturing tissue, for treating a hernia or as a tissue plug, for treating burns and dermabrasion, as well as other conditions described below.

In any of the embodiments above, the ECM is or can be isolated.

BRIEF DESCRIPTION OF THE FIGURES

FIG. 6 presents ELISA data for DNA content in pre- and post-processed axotol tissue, with comparison data from human amniotic membrane tissue.

DETAILED DESCRIPTION OF THE PREFERRED EMBODIMENTS

Definitions

Figure 1:
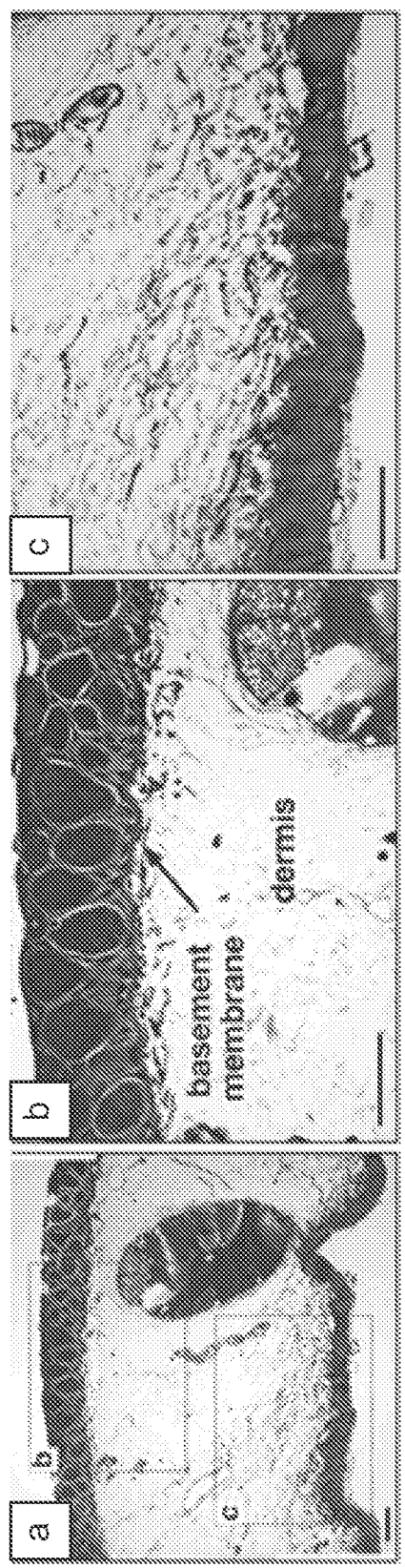
FIG. 1 shows native axolotl tissue samples prepared for histological examination, to identify EC elements.

"Antimicrobial polypeptides" (or "AMPs") means small peptides of variable length, sequence and structure with broad spectrum activity against a wide range of microorganisms including bacteria, viruses, fungi, protozoa, parasites, prions, and tumor/cancer cells. (See, e.g., Zaiou, J Mol Med, 2007; 85:317; herein incorporated by reference in its entirety). AMPs have broad-spectrum of rapid onset of killing activities, with potentially low levels of induced resistance and concomitant broad anti-inflammatory effects. Anti-microbial polypeptides include defensins, such as a-defensins (e.g., neutrophil defensin 1, defensin alpha 1, neutrophil defensin 3, neutrophil defensin 4, defensin 5, defensin 6), β-defensins (e.g., beta-defensin 1, beta-defensin 2, beta-defensin 103, beta-defensin 107, beta-defensin 110, beta-defensin 136), and θ-defensins. Anti-microbial polypeptides include cathelicidins such as hCAP18.

"Biocompatible" means that a composition and its normal degradation products in vivo are substantially non-toxic and non-carcinogenic in a subject within useful, practical and/or acceptable tolerances.

"Cytocompatible" means that a composition can sustain the viability and growth of a population of cells.

"Decellularized ECM" means extra cellular matrix sufficiently free of cellular components to eliminate or reduce antigenicity of the extra cellular matrix to an extent where the matrix would be considered non-toxic as a xenograft.

"Isolated" when used in connection with the ECM of the invention means separated from other Urodele tissue.

"Non-toxic" means that a composition, when implanted in a subject, causes little or no adverse reaction or substantial harm to cells and tissues in the body, and does not cause a substantial adverse reaction or substantial harm to cells and tissues in the body, for instance, the composition does not cause necrosis, an infection, or a substantial immune response resulting in harm to tissues from the implanted or applied composition.

"Progenitor cell" means a cell that can differentiate under certain conditions into a more-differentiated cell type. Non-limiting examples of progenitor cells include stem cells that may be totipotent, pluripotent, multipotent stem cells, or referred to as progenitor cells. Additional non-limiting examples of progenitor cells include perivascular stem cells, blastema cells, and multilineage progenitor cells.

"Retain structural and functional integrity" used in connection with the ECM of the invention means retaining sufficient structure and function to permit and support the use of the matrix as a substrate for the growth of cells in vivo or in vitro.

"Subject" means an animal. In some embodiments the animal is a mammal. The mammal can be a dog, cat, a horse, a cow, a goat, a sheep, a pig or a non-human primate. In any embodiment the mammal can be a human.

"Treatment" or "treating" means administration or application to a subject by any suitable dosage means, regimen and route of a composition with the object of achieving a desirable clinical/medical end-point, such as assisting in wound healing, tissue closure, bulking tissue, preventing tissue adhesion, providing structural support to tissue, providing a protective barrier, correcting a defect, etc.

"Urodele fraction derived from decellularized Urodele ECM" means an extract or isolate of decellularized Urodele ECM maintaining sufficient characteristics of a Urodele in terms of chemical structure and/or relative chemical concentrations of two (or three, or four, or five or more) chemical entities in the extract or isolate to distinguish the extract as obtained from a Urodele by any one or more of electron microscopy, HPLC, immunohistochemistry, and the like.

General Preparative Methodology

According to the invention, urodele tissue samples obtained for decellularization can be treated in the manner detailed in US 2008/0046095 or US 2010/0104539. Thus, tissue samples may be subjected to cleaning and chemical decontamination. In this manner, a tissue sample is washed for approximately 10 to 30 minutes in a sterile basin containing 18% NaCl (hyperisotonic saline) solution that is at or near room temperature. Visible cellular debris, such as epithelial cells adjacent to the tissue basement membrane, is gently scrubbed away using a sterile sponge to expose the basement membrane. Using a blunt instrument, a cell scraper or sterile gauze, any residual debris or contamination also is removed. Other techniques including, but not limited to, freezing the membrane, physical removal using a cell scraper, or exposing the cells to nonionic detergents, anionic detergents, and nucleases also may be used to remove cells.

In one embodiment, urodele tissue is decellularized using alkaline treatment.

The tissue is placed into a sterile container, such as a Nalgene jar, for the next step of chemical decontamination. Thus, each container is aseptically filled with 18% saline solution and sealed (or closed with a top). The containers then are placed on a rocker platform and agitated for between 30 and 90 minutes, which further cleans the tissue of contaminants.

In a sterile environment using sterile forceps, the tissue is gently removed from the container containing the 18% hyperisotonic saline solution and placed into an empty container. This empty container with the tissue is then aseptically filled with a pre-mixed antibiotic solution. Preferably, the premixed antibiotic solution is comprised of a cocktail of antibiotics, such as Streptomycin Sulfate and Gentamicin Sulfate. Other antibiotics, such as Polymixin B Sulfate and Bacitracin, or similar antibiotics available now or in the future, are suitable as well. It is preferred that the antibiotic solution be at room temperature when added so that it does not change the temperature of or otherwise damage the tissue. This container containing the tissue and antibiotics is then sealed or closed and placed on a rocker platform and agitated for, preferably, between 60 and 90 minutes. Such rocking or agitation of the tissue within the antibiotic solution further cleans the tissue of contaminants and bacteria.

In a sterile environment, the container is opened and, using sterile forceps, the tissue is gently removed and placed in a sterile basin containing sterile water or normal saline (0.9% saline solution). The tissue is allowed to soak in place in the sterile water/normal saline solution for at least 10 to 15 minutes. The tissue may be slightly agitated to facilitate removal of the antibiotic solution and any other contaminants from the tissue.

In some cases, the present invention involves treating urodele tissue using a chemical sterilization methodology, as illustrated the Tutaplast® and Allowash® procedures, optionally in combination with mechanical processes that gently agitate chemical agents, as in the BioCleanse® system. Thus, urodele tissue is subjected to oxidative and/or alkaline treatments as well as osmotic treatment to break down cell walls, to inactivate pathogens, and to remove bacteria. In addition, tissue may be subjected to delipidization, solvent dehydration (to permit room temperature storage of tissue without damaging the collagen structure) and/or low-dose gamma irradiation to ensure sterility of the final product.

Efficient cell removal upon decellularization can be verified by various known means, including histological analyses to detect nuclear and cytoplasmic structures, immunohistochemical or immunofluorescent assaying for indicative intracellular proteins, and DNA detection. The nature of desirable components in the final urodele-derived scaffold biomaterial varies depending on the clinical indication being treated. Once a particular indication is identified, the knowledgeable clinician can determine which components in the urodele tissue sample should be retained in the final scaffold product, and standard methodology can be employed to ensure that the desired components are present following decellularization.

Samples may be viewed histologically before, during, and/or after decellularization to monitor the process and to confirm that the desired degree of cellular component removal is reached. For instance, tissues can be analyzed for cytoskeletal content to gauge sufficient decellularization. Intracellular protein content also may be assayed to determine if decellularization is sufficient. In addition, the tissue sample thickness and chemical makeup may be monitored to determine when sufficient decellularization has been achieved. Periodic monitoring during processing allows for a real time response to the observed tissue properties.

In some cases, a sufficiently decellularized tissue comprises no more than 50 ng dsDNA per mg ECM dry weight. Alternatively, for some indications, a sufficiently decellularized tissue lacks visible nuclear material in a tissue section stained with 4',6-diamindino-2-phenylindole (DAPI) or haematoxyilin and eosin (H&E).

In scenarios where removal of an adjacent epithelial cell layer is required, the presence or absence of epithelial cells remaining in the sample can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification. The presence of cells and cellular material will appear darker than the areas which have been de-epithelialized.

Once cellular removal has progressed sufficiently, conventional methods are employed to confirm the retention of desired structural and functional properties of the remaining ECM scaffold. The specific structural testing that should be conducted depends on the intended clinical application of the final scaffold product. In some cases, the urodele tissue starting material may be monitored before, during, and after decellularization to ensure that the desired structural components and configuration are maintained in the final product.

One method for determining whether the desired ECM components are present involves staining parallel tissue sections and examining them histologically to determine whether the desired constituents and structural orientation of the urodele tissue have been preserved. For instance, urodele tissue can be stained with H&E and immunoperoxidase stain for laminin to assess preservation of ECM and laminin. In general, the three-dimensional configuration of ECM components remaining in the final biomaterial scaffold product should approximate that of pre-decellularized material when viewed via histological staining. Another component one can assay for is AMPs, as the ECM of the invention is rich in AMPs.

Accordingly, the urodele-derived biomaterial of the invention comprises ECM components useful for directing enhanced re-epithelialization and promoting efficient tissue regeneration or wound healing. The inventive biomaterial also serves as a matrix and reservoir for bioactive peptides such as growth factors, adhesion proteins and AMPs. Accordingly, the biomaterial functions effectively as a biological scaffold for tissue regeneration, providing both the necessary bioactive stimulation and structural support. The product can be used as is, cut into smaller pieces or shapes, laminated to itself or other materials, pre-punctured to provide openings for securing attachments, formed into desired three dimensional shapes, as well as other formats, discussed in more detail below.

Powders and Gels

In embodiments, the scaffold can be further processed into small grains or a powder. The fine particles can be hydrated in water, saline or a suitable buffer or medium to produce a paste or gel. This fine material, paste or gel produced from it may be used for a multitude of purposes, described in greater detail below.

Although numerous methods exist, two exemplary methods may be used to produce a particulate form of the scaffold. The first method involved lyophilizing the disinfected material and then immersing the sample in liquid nitrogen. The snap frozen material is then reduced to small pieces with a blender so that the particles are small enough to be placed in a rotary knife mill, such as a Wiley mill. A #60 screen can be used to restrict the collected powder size to a desired size, for example less than 250 mm. A Sonic sifter or other classification device can be used to remove larger particles and/or to obtain a particle size distribution within a desired range. A second method is similar to the previous method except the sample is first soaked in a 30% (w/v) NaCl solution for 5 min. The material is then snap frozen in liquid nitrogen to precipitate salt crystals, and lyophilized to remove residual water. This material is then comminuted as described in above. By precipitating NaCl within the sample, it is expected that the embedded salt crystals would cause the material to fracture into more uniformly sized particles. The particles are then suspended in deionized water and centrifuged for 5 min at 1000 rpm three times to remove the NaCl. The suspension is snap frozen and lyophilized again. Finally, the powder is placed in a rotary knife mill to disaggregate the individual particles.

The powder can be hydrated to create a gel, with or without other gelling materials to supplement gelling.

The powder, paste or gel can be applied without further processing to treat a subject. It can be sprayed, painted, injected or otherwise applied to a wound or surgical site. The gel can be shaped. The powder, paste or gel also can be placed inside a "bag", such as a polymeric synthetic material or a ECM sheet as described herein to produce a larger three-dimensional structure, such as an orthopedic implant for cartilage repair (e.g., knee or TMJ cartilage repair) or an implant for breast reconstruction or augmentation. In such a case, a bag of a desirable size and shape is formed from sheets of ECM material or other biocompatible polymeric material, and then the bag or cover can be filled with the tissue-derived powder or gel described herein. The shape of the device or implant can vary with its intended use. The bag may be molded into a useful shape by any useful molding technique, such as the shape of cartilage for the ear, nose, knee, TMJ, rib, etc., prior to filling the molded bag with the scaffold material described herein. In one example, a biodegradeable polymeric matrix (e.g., PEUU or PEEUU) is sprayed or electrodeposited onto a mold. The resultant molded cover can then be filled with the material. Heat, for example, may be used to seal the cover.

Additives

In another embodiment, at least one agent xenogenic to a Uroldele is added to the ECM or Urodele fraction thereof before it is implanted in the subject, otherwise administered to the subject or used in cell culture. Generally, the agents include any agent useful in cell culture or as a therapeutic or therapeutic adjuvant. The agents can be coated on, infused into or otherwise covalently or non-covalently attached to or incorporated onto or into the ECM of the invention. The agents also can be otherwise combined with a product that contains the ECM, for example, as by mixing powders of the agent and ECM together. Each agent may be used alone with the ECM of the invention or in combination with other agents. Non-limiting examples of such agents include anti-microbial agents, growth factors, cytokines, chemokines, emollients, retinoids, steroids, and cells, including but not limited to the subject's own cells.

In certain non-limiting embodiments, the agent is a growth factor. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors.alpha. and .beta. (TGF-.alpha. and TGF-.beta.), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain non-limiting embodiments, the therapeutic agent is an antimicrobial agent, such as, without limitation, an anti-microbial peptide, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting embodiments, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin.

Other drugs that may promote wound healing and/or tissue regeneration may also be included.

The agent may be dispersed within the scaffold by any useful method, e.g., by adsorption and/or absorption. For example, the therapeutic agent may be dissolved in a solvent (e.g., DMSO) and added to the scaffolding. In another embodiment, the agent is mixed with a carrier polymer (e.g., polylactic-glycolic acid microparticles, agarose, a poly(ester urethane) urea elastomer (PEUU) or a poly(ether ester urethane) urea elastomer (PEEUU)), which is subsequently dispersed within or applied to the scaffold. By blending the agent with a carrier polymer or elastomeric polymer, the rate of release of the therapeutic agent may be controlled by the rate of polymer degradation and/or by release from the polymer by diffusion or otherwise. Likewise, a therapeutic agent may be provided in any dissolvable matrix for extended release, as are known in the pharmaceutical arts, including sugar or polysaccharide matrices. The agent also may be included with the powdered ECM and gelled with the powdered ECM. The agent may be covalently attached to the ECM of the invention. The foregoing are meant to be non-limiting examples.

Extracts

In addition to the decellularized ECM in its native state or ground as a particulate or powder, the invention also provides extracts and isolates of the same. As mentioned above, the Urodele ECM is loaded with antimicrobial peptides, growth promoting factors, collagen and laminins, and Urodele fractions of the ECM are useful according to the invention.

Extraction buffers are well known in the art. One such buffer is 4 M guanidine and 2 M urea each prepared in 50 mM Tris-HCl, pH 7.4. The powder form of the ECM can be suspended in the relevant extraction buffer (e.g., 25% w/v) containing phenylmethyl sulphonyl fluoride, N-ethylmaleimide, and benzamidine (protease inhibitors) each at 1 mM and vigorously stirred for 24 hours at 4° C. The extraction mixture can then be centrifuged and the supernatant collected. The insoluble material can be washed in the extraction buffer, centrifuged, and the wash combined with the original supernatant. The supernatant can be dialyzed against deionized water. The dialysate can then be centrifuged to remove any insoluble material and the supernatant used immediately or lyophilized for long term storage. Such an isolate will contain growth factors in concentrations specific to Urodeles.

In another aspect, the extraction is done by conditioning medium. A method of making Urodele tissue-specific extract by taking the powdered ECM, forming a solution thereby generating a supernatant and a particulate, wherein the supernatant is an extract and isolating the extract from the particulate. One also could grow cells on the ECM, and isolate the supernatant after a period of time of cell growth.

Synthetic Materials

Synthetic biocompatible and cyto-compatible material can be combined with the ECM, such as, for example, (a) a structural support for a sheet or a gel of the ECM, (b) a structural support for shaping the ECM, (c) a coating for the ECM (or a coating containing the particulate ECM), a supplemental gelling agent, or (d) a sustained release material for the particulate ECM or an isolate thereof. Such polymers have been known to be applied to other ECM materials as a backing sheet, including materials that are themselves biodegradable. Suitable synthetic material for a matrix can be biocompatible to preclude migration and immunological complications, and can be able to support cell growth and differentiated cell function. Some are resorbable, allowing for a completely natural tissue replacement. Some can be configurable into a variety of shapes and have sufficient strength to prevent collapse upon implantation. Studies indicate that the biodegradable polyester polymers made of polyglycolic acid fulfill all of these criteria (Vacanti, et al. J. Ped. Surg. 23:3-9 (1988); Cima, et al. Biotechnol. Bioeng. 38:145 (1991); Vacanti, et al. Plast. Reconstr. Surg. 88:753-9 (1991)). Other synthetic biodegradable support matrices include synthetic polymers such as polyanhydrides, polyorthoesters, and polylactic acid. Further examples of synthetic polymers and methods of incorporating or embedding cells into these matrices are also known in the art. See e.g., U.S. Pat. Nos. 4,298,002 and 5,308,7.

As a non-limiting example, the powder may be formulated with tri-block co-polymers. See international pubished application WO2012131104 and WO2012131106, each of which is incorporated herein by reference in its entirety. Other examples include poloxamers, which are nonionic triblock copolymers composed of a central hydrophobic chain of polyoxypropylene (poly(propylene oxide)) flanked by two hydrophilic chains of polyoxyethylene (poly(ethylene oxide)). Poloxamers are also known by the trade name Pluronics (BASF). Certain poloxamers are useful as sustained release materials for pharmaceuticals.

Particles of the invention also may be encapsulated into a polymer, hydrogel and/or surgical sealant. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.). In another embodiment, the particle may be encapsulated into any polymer known in the art which may form a gel when injected into a subject. As another non-limiting example, the particle may be encapsulated into a polymer matrix which may be biodegradable. Additional examples of polymers for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®.

Uses

The decellularized ECMs described herein are useful for growing cells, tissues, organs in virtually any in vivo, ex vivo, or in vitro use. The ECMs can be used as a substrate to facilitate the growth and/or differentiation of cells. In vitro, the ECMs are useful as a cell growth substrate to support the growth in culture of cells, including virtually any type of cells or cell-lines, including stem cells, progenitor cells or differentiated cells. In one embodiment, the cells are cancer cells. In one embodiment, the cancer cells form nodules when grown on the ECMs. Cells on the substrate also may be grown into tissue, organ or body part precursors, or even mature tissues or structures. Cells grown on ECMs may be used for implantation, for wound dressings, for in vitro drug testing, for modeling differentiation, etc. The cells may be matched in tissue cell type to the ECM or unmatched. The cells are xenogenic.

The ECM of the invention is useful in vivo as a cell growth scaffold for tissue growth for any useful purpose, including repair, replacement or augmentation of tissue in a subject in either humans or animals. For example, the materials are useful in repair and/or replacement of tissue lost or damaged during trauma or surgery, for example in loss of tissue after tumor removal. The materials are useful for structural repair, such as inguinal hernia repair, parastomal reinforcement, soft tissue reinforcement, surgical stapleline reinforcement during, for example, bariatric surgery or lung resection, umbilical hernia grafts, Peyronie's repair grafts, incision grafts and fistula plugs. The materials are useful for wound dressings, such as for burns, graft and split-thickness graft coverings, ulcers including decubitis ulcers and dermal abrasion procedures. The materials are useful for cosmetic purposes, for example in breast, lip or buttock augmentation. An aspect of the invention particularly appealing for anti-adhesion surgical uses is the properties of the basement membrane, which inhibit or prevent adhesion. The presence of the AMPs make the ECM of the invention particularly well suited for the foregoing applications.

As mentioned above, the materials described herein can be molded or contained within a structure to form desired shapes, such as, for cartilage repair or replacement by seeding the material with, e.g., chondrocytes and/or chondroprogenitor cells. The materials can be ground into a powder and used to reconstitute and/or form gels, as cell culture additives, as a powder, spray, liquid, suspension or coating for application to (a) a wound, (b) an implant, (c) a wound dressing, etc.

In one embodiment, for example, adipose stem cells are propagated in the cell growth scaffolds described herein. Adipose stem cells are of mesodermal origin. They typically are pluripotent, and have the capacity to develop into mesodermal tissues, such as: mature adipose tissue; bone; heart, including, without limitation, pericardium, epicardium, epimyocardium, myocardium, pericardium, and valve tissue; dermal connective tissue; hemangial tissues; muscle tissues; urogenital tissues; pleural and peritoneal tissues; viscera; mesodermal glandular tissues; and stromal tissues. The cells not only can differentiate into mature (fully differentiated) cells, they also can differentiate into an appropriate precursor cell (for example and without limitation, preadipocytes, premyocytes, preosteocytes). Also, depending on the culture conditions, the cells can also exhibit developmental phenotypes such as embryonic, fetal, hematopoetic, neurogenic, or neuralgiagenic developmental phenotypes.

In one embodiment, a subject's own cells are dispersed within the matrix. For example, in the production of cartilaginous tissue, chondrocytes and/or chondroprogenitor cells can be dispersed within the matrix and optionally grown ex vivo prior to implantation. Likewise, skin cells of a subject can be dispersed within the scaffolding prior to implantation on a damaged skin surface of a subject, such as a burn or abrasion.

When used as a gel, a non-limiting example is injecting the gel into a subject at a desirable site, such as in a wound. In one instance, the gel can be injected in a bone breakage or in a hole drilled in bone to facilitate repair and/or adhesion of structures, such as replacement ligaments, to the bone. In another use, finely comminuted particles can be sprayed onto a surface of a subject, such as in the case of large surface abrasions or burns. The scaffold can also be sprayed onto skin sutures to inhibit scarring. The ECM of the invention can be place or sutured in place inside the body at a surgical site such as mentioned above. All of these treatments are embraced by the present invention.

Urodele decellularized ECM can be used also for sustained delivery of therapeutic molecules, proteins or metabolites, to a site in a host. See, for example, U.S. 2004/0181240, which describes an amniotic membrane covering for a tissue surface which may prevent adhesions, exclude bacteria or inhibit bacterial activity, or to promote healing or growth of tissue, and U.S. Pat. No. 4,361,552, which pertains to the preparation of cross-linked amnion membranes and their use in methods for treating burns and wounds. The ECMs of the invention can be used in the same manner.

Pharmaceutical Formulations

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

The pharmaceutical compositions described herein may be prepared by any method known in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-use configuration.

The ECM in accordance with the invention may be prepared, packaged, and/or sold in bulk, as a single unit dose, and/or as a plurality of single unit doses. For example, the composition may comprise between 0.1% and 100% (w/w) of the ECM. When other active agents are included, relative amounts of agents combined with the ECM of the invention will be known to those of ordinary skill in the art, similar to those amounts used in combination with ECM as formulated in the prior art. Relative amounts also may vary, depending upon the identity, size, and/or condition of the subject being treated and further depending upon the route by which the ECM is to be administered.

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art. See Remington: THE SCIENCE AND PRACTICE OF PHARMACY ($21^{st}$ Ed.), A. R. Gennaro, Lippincott, Williams & Wilkins (Baltimore, Md., 2006); incorporated herein by reference in its entirety.

EXAMPLES

Example 1. Processing Axolotl Dermis

Axolotl dermis samples can be decellularized by preparing excised samples from healthy or healing axolotl dermal tissue and then subjecting the samples to hypo/hyperosmotic soaks for cell lysis, solvent dehydration, and oven drying. Specific processing of these grafts includes storage in 15-26% NaCl, multiple hypo/hyperosmotic soaks (utilizing NaCl solutions and water), and then solvent dehydration using ethanol, and then evaporation of the solvent either with air drying or oven drying at 37° C.

Figure 2:
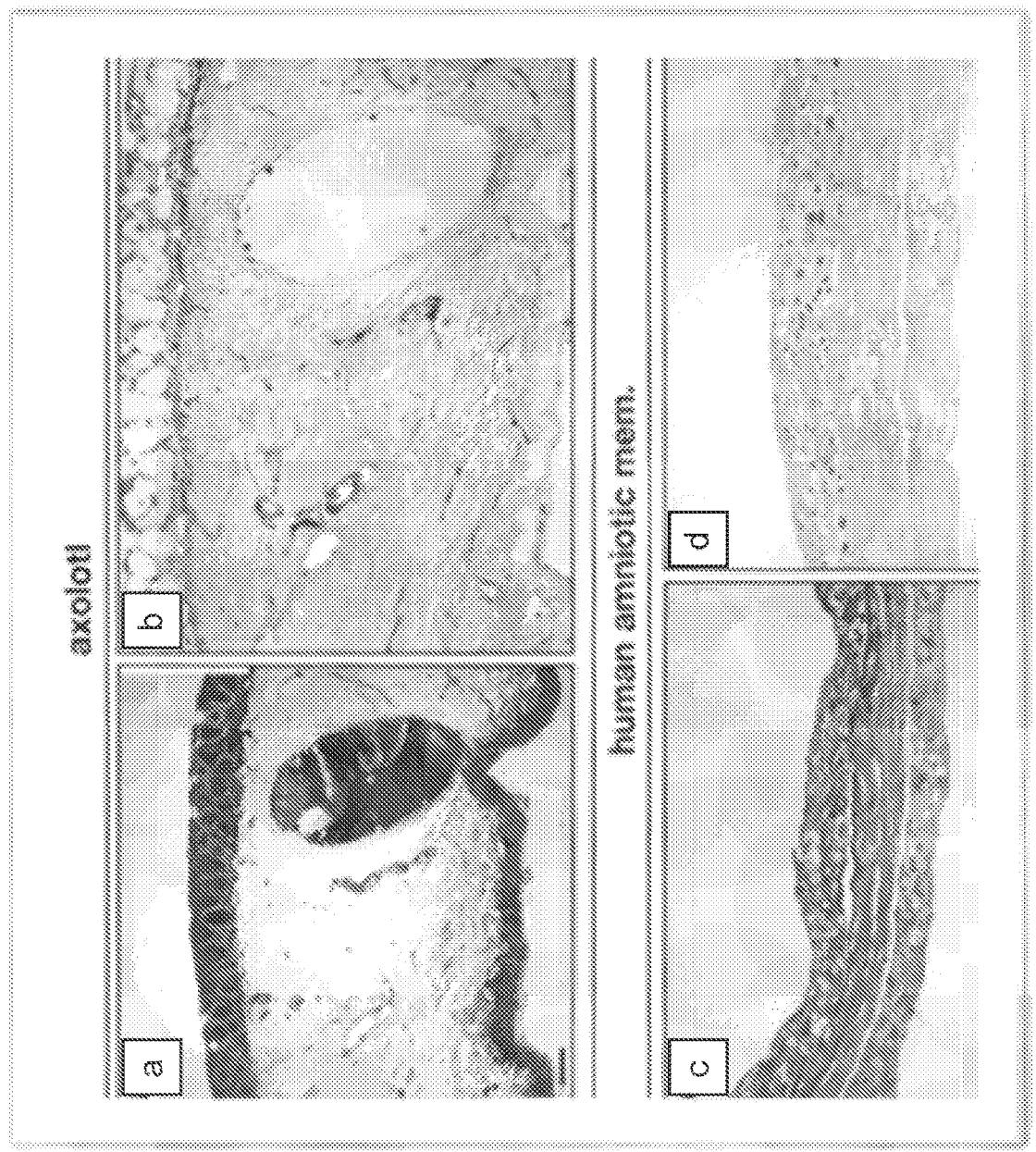
FIG. 2 hematoxylin and eosin (H&E) and Alcian Blue staining of native axolotl dermal tissue and human amniotic membrane (40× magnification).
Figure 3:
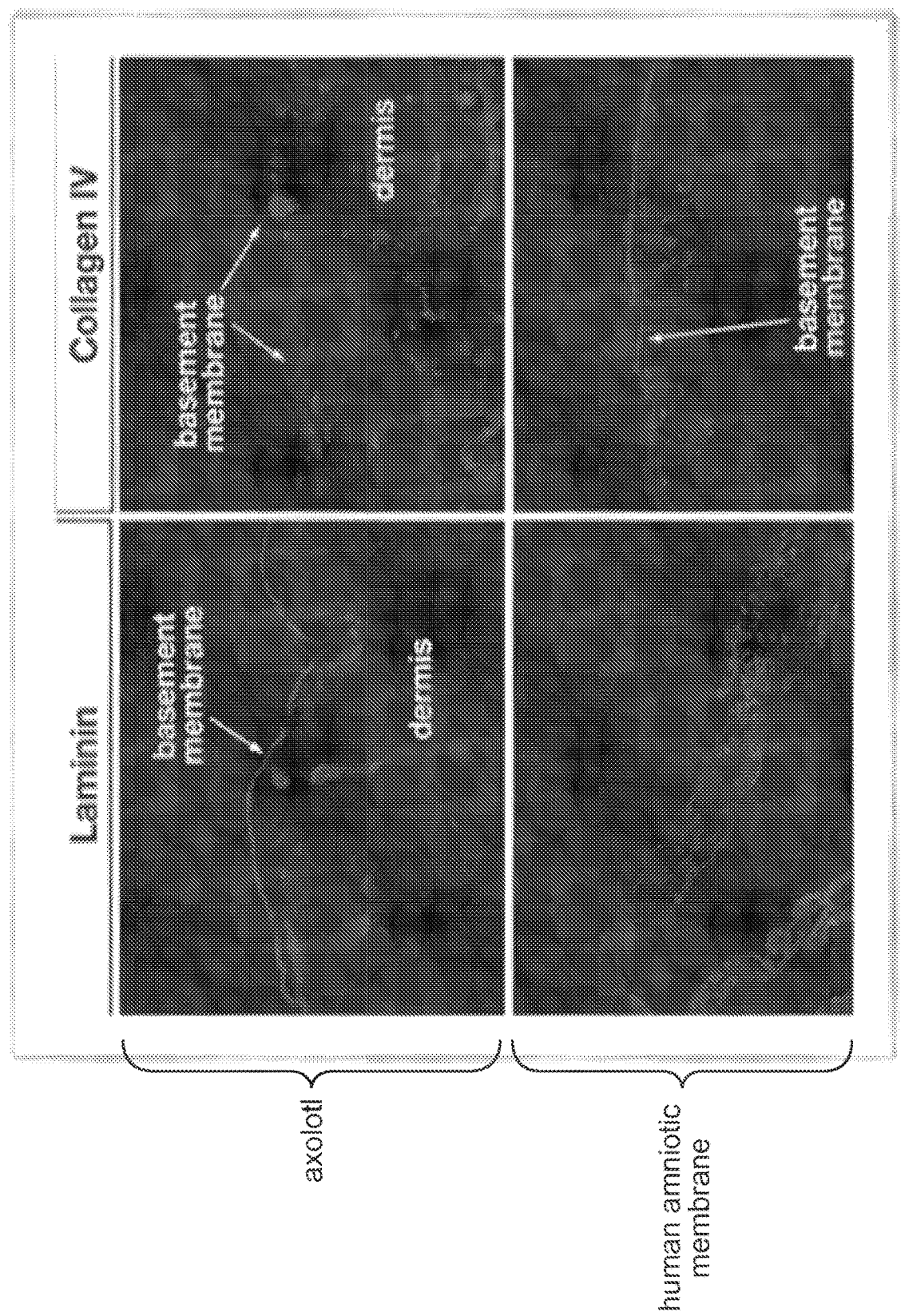
FIG. 3 shows immunohistocemical staining via species-specific collagen IV and laminin antibodies of native axolotl dermal tissue and human amniotic membrane tissue, at 40× magnification.
Figure 4:
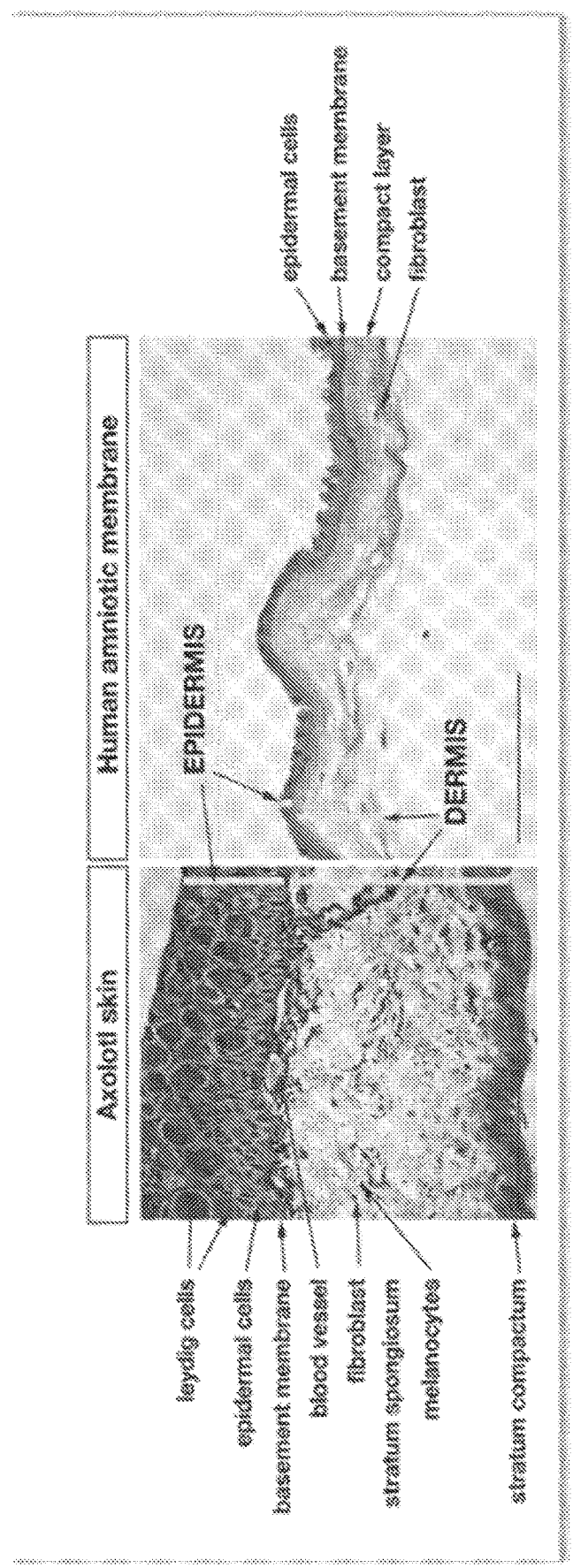
FIG. 4 depicts axolotl skin and human amniotic membrane samples prepared for histological examination, to identify EC elements.
Figure 5:
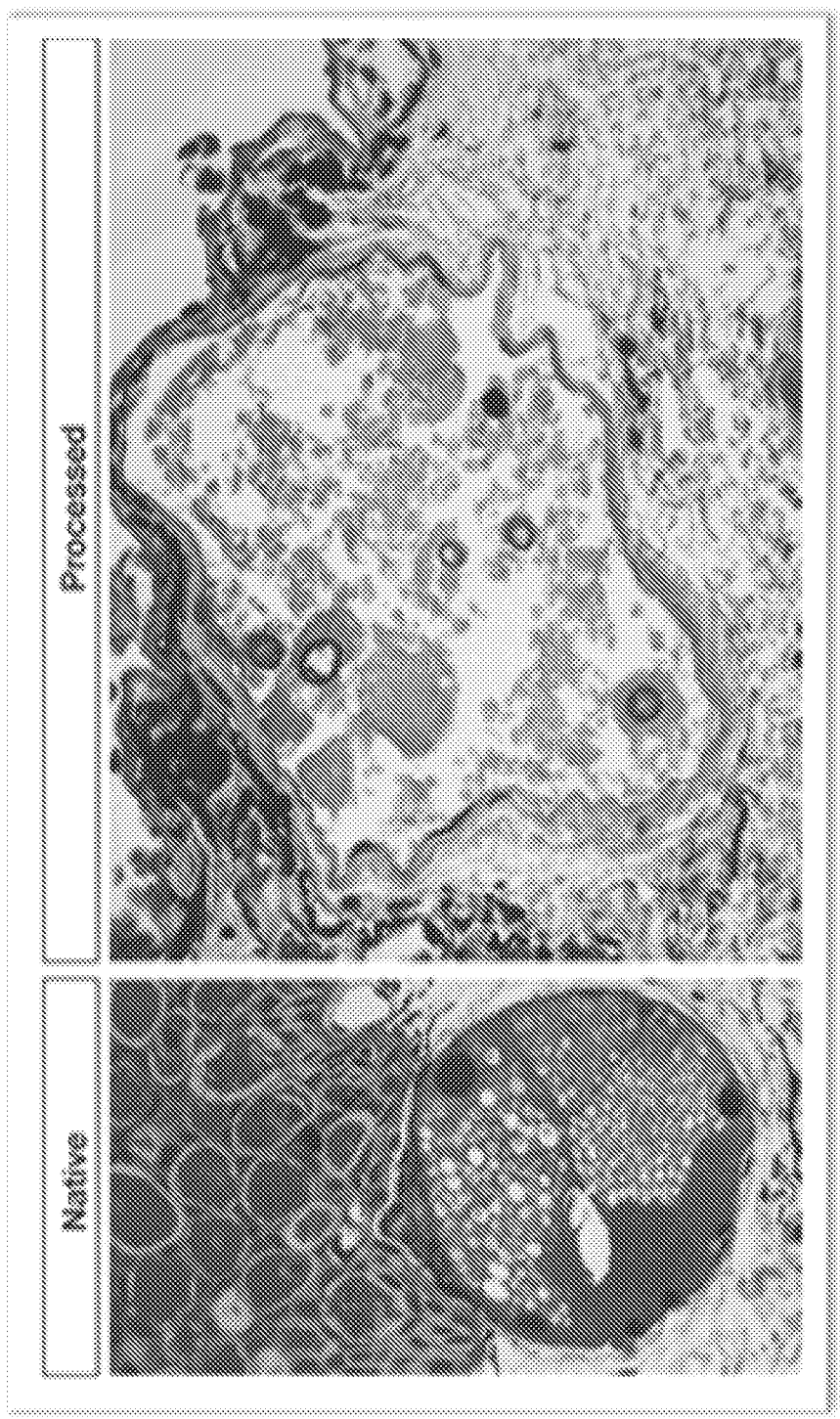
FIG. 5 illustrates a histological evaluation of H&E-stained, paired native and post-processed sections of axolotl dermal tissue.

Histological examination of native axolotl dermal tissue was performed to identify the presence of the notable ECM elements, such as the basement membrane. See FIG. 1 and FIG. 4. Comparative histological and immunohistochemical analysis of native axolotl dermal tissue and human amniotic membrane was performed to compare the ECM structure and constituents, and to assess relative concentration and distribution of critical constituents. See FIG. 2, FIG. 3, and FIG. 4. FIG. 3 shows immunohistocemical staining via species-specific collagen IV and laminin antibodies of native axolotl dermal tissue and human amniotic membrane tissue, at 40× magnification. FIG. 2 shows H&E and Alcian Blue staining (40×) of native axolotl dermal tissue and human amniotic membrane, and it demonstrates the comparable histoarchitecture and presence of sulfated glycosaminoglycans in both tissues. Histological evaluation with hematoxylin and eosin-stained, paired native and post-processed sections of axolotl dermal tissue (see FIG. 5) showed post-process preservation of the extracellular matrix histoarchitecture and the absence of cells or any significant concentration of cellular debris.

Example 2. Splitting and Lamination of Acellular Dehydrated Axolotl Dermis

Decellularized dehydrated axolotl dermis can be split, via a mechanical splitter, to isolate heterogeneous matrix into homogenous sections. Isolated sections of desired thickness then can be rehydrated and lyophilized to obtain multilayered laminate structures of desired orientation with facial surface features. More specifically, dual-sided basement membrane structure, with interior open porous matrix obtained from the reticular dermis region of the dermal matrix, can be constructed to obtain desired facial surface properties. Alternatively, isolated native section can be used in native form for desired clinical outcome. For example, open porous homogenous matrix of the reticular dermis can be used to obtain augmentation of soft tissue structures.

A laminated custom construct with sulfated gags on both facial surface and collagen IV and laminin could be obtained for desirable dual-surface, anti-adhesion and antimicrobial properties for clinical benefit. In addition, multilayer structures could be constructed to prolong in vivo durability of the graft.

Example 3. Preparation of Solubilized Acellular Dehydrated Axolotl Dermis, Pericardium, Fascia Lata, Periosteum, Peritoneum, or Dura Mater Decellularized dehydrated axolotl native or isolated section of acellular urodele connectivue tissue matrix can be prepared by sectioning decellularized soft tissue structures into 1 $cm^2$ sections and homogenizing the sections in a Warring blender (~100 grams of tissue) in aqueous 1M glacier acetic acid for 30-60 seconds. Preparation of sponge can be obtained by the addition of varying volumes of water followed then neutralization and lypoholization of the slurry in a mold of desired geometric shape. The resultant porosity will correlate to the volume of water added to the matrix. Additionally, a selected range of bioactive extracts can be added to the slurry prior to neutralization, including particulated or small protein constituents extracted from digested human or urodele mineralized and nonmineralized connective tissues, such as demineralized bone matrix, elastin, or bone morphogenic proteins, which can be covalently loaded into constructs. Extracts will be covalently bound with collagen fibers after neutralization and return to physiological condition where fibrillogenisis will occur. Subsequent release of bioactive constituents will occur during proteolyctic degradation in vivo and ensure molecules are not consume or exposed during acute inflammation in vivo. Alternatively, aqueous NaCl can be added to the slurry, prior to neutralization, to obtain a sustained, low viscosity solution for injection, which is stable at room temperature. Injection of slurry through ion-selective membrane will remove salt ions and permit for fibrillogenisis to occur post injection and formation of three-dimensional matrix.

Example 4. Preparation of Sterilized Particulated or Powder Form of Mineralized and Non-Mineralized Decellularized and Dehydrated Urodele Connective Tissue Matrix Following decellularization of sections of mineralized collagen urodele connective tissue, one can perform a demineralization process, similar to that employed by Urist, and solvent or lyophilization dehydration, cryomilling of sectioned acellular demineralized, mineralized, or non-mineralized urodele connective tissue extracellular matrix, thereby to obtain particulated or powder form of the ECM with preserved histoarhictiecutre and function. The final particle size distribution can be varied depending on duration and sieving, post-cyromilling, between 125 and 850 microns. Low-dose cold gamma irradiation or e-beam irradiation (<25 Kgy) can be employed to sterilize acellular ECM sheets, particulate or powder and custom engineered constructs.

Example 5. In Vitro Characterization of Acellular Mineralized and Non-Mineralized Urodele Healthy or Healing Connective Tissue Matrix Through a series of in vitro analyses one can verify decellularization and preservation of native or custom engineered functional and structural properties of decellularized extracellular matrix constructs and/or particulate, including multilayer laminated constructs such as a dual-sided basement membrane sheet matrix or isolated native homogenous open porous matrix or solubilized, lyophilized and loaded ECM-derived collagen sponge. DNA content, as a marker for cell debris, can be employed to assess decellularization quantitatively, using a single, ethanol-based extraction technique with a fluorometric dye, Quant-iT PicoGreen (Molecular Probes, USA), in a ratio of 170 µL working solution to 30 µL samples/standards in a 96-well plate. Paired native and post-processed analysis and comparison to commercially available tissue ECM's can be performed to verify acceptability. See FIG. 6.

ELISA analysis for quantification of bioactive constituent and native and post process protelyctic resorption profiles can be performed. Upon digestion with collagenase (232-262 mg/unit activity), normalized-weight-to-surface-area sections of decellularized and dehydrated urodele ECM tissue or constructs (Sigma, USA), in a pH 7.6 buffer (50 mM Tris-HCl, 200 mM $CaCl_2$, 50 mM NaCl) for 24 hours at 37° C., can be analyzed at various time points to construct a relative resorption curve of pre- and post-process tissue to verify preservation of histoarchitecture. Solubilized collagen following digestion can be assessed, using a Sircol kit (Biocolor Ltd., UK), in 100 µL aliquots of acid/salt-washed digests. Specifically, levels of BMP 2/4 and TGF-1 growth factors or sulfated gags can be assessed, following digestion, by means of commercially available ELISA kits (R&D Systems, Minneapolis, Minn.). Protein content in 1:10 dilution digests can be measured via a standard Bradford absorbance assay.

Microscopic evaluation of samples can be performed using fixation in 4% paraformaldehyde and paraffin embedding, sectioning at 5 µm, and routine histological staining (Histoserv, Inc., USA). Longitudinal cross sections can be stained with hematoxylin and eosin. Images can be acquired and analyzed using standard brightfield techniques on an Olympus IM inverted microscope. Samples can analyzed using scanning electron microscopy after dehydration in a graded ethanol series (15%, 30%, 50%, 70%, 95%, and 100%), critical-point drying in $CO_2$, and sputter coating with gold. Samples can be visualized in an FEI Quanta 600 FEG scanning electron microscope, and representative images of scaffold ultrastructure can be acquired.

Direct cell contact methodology (ISO10993, Part 5), for qualitative cell viability assessment at 24 hours, can be conducted for cytotoxicity testing and at extended time points (48 and 72 hours) to gauge cell proliferation and adhesion efficiency. A manual count of non-adherent cells in a hemocytometer, following transfer and trypsinization of the culture wells, can be conducted. A CellTiter 96 assay can performed to quantify viable cells after four days. A live/dead cell staining kit can used as well to visualize scaffolds via fluorescence microscopy at 24 hours and day four, thereby to verify biocompatibility.

The invention claimed is:

1. A tissue graft comprising extracellular matrix components derived from a Urodele, said tissue graft derived by:
    a. obtaining a tissue sample from a urodele, which tissue sample comprises extracellular matrix; and
    b. decellularizing said tissue sample to produce decellularized extracellular matrix by removing sufficient cellular components of the sample to reduce or eliminate antigenicity of the biomaterial making it suitable for use as a xenograft.

2. The tissue graft of claim 1, wherein said decellularizing comprises subjecting said tissue sample to an alkaline treatment.

3. The tissue graft of claim 2, wherein said process further comprises subjecting said sample to sterilization.

4. The tissue graft of claim 1, wherein the Urodele is an Axolotl.

5. A tissue graft according to claim 1 comprising sterile, isolated, decellularized Urodele extra cellular matrix (ECM), wherein the ECM is a powder, a paste, a gel, a sheet, or a mesh, and wherein the ECM is parietal ECM, mesothelial ECM, thoracic cavity ECM, abdominal cavity ECM, pericardium ECM or dermal tissue ECM.

6. The tissue graft of claim 5, wherein the ECM is a powder.

7. The tissue graft of claim 6, wherein the powder has a particle size between 125 and 850 microns.

8. The tissue graft of claim 6, wherein the powder has a particle size of less than 250 microns.

9. The tissue graft of claim 5, wherein the ECM is a paste.

10. The tissue graft of claim 5, wherein the ECM is a gel.

11. The tissue graft of claim 10, wherein the gel comprises a synthetic polymer.

12. The tissue graft of claim 5, wherein the ECM is a mesh.

13. The tissue graft according to claim 5 wherein the Urodele ECM is Axolotl ECM and is in a form selected from the group consisting of: a powder; a paste; a gel; a mesh; a sheet of parietal ECM, mesothelial ECM, thoracic cavity ECM, abdominal cavity ECM, pericardium ECM or dermal tissue ECM, and wherein the sheet of ECM is infused with, coated with, or attached to an agent xenogeneic to a Urodele that is a growth factor, a cytokine, a chemokine, a protein, a carbohydrate, a sugar, a steroid, an antimicrobial agent, a synthetic polymer, an adhesive, or a drug; and at least two sheets of isolated Urodele decellularized ECM laminated to one another.

14. A tissue graft according to claim 1 comprising sterile, isolated, decellularized Urodele extra cellular matrix (ECM), wherein the ECM is a sheet, wherein the ECM is parietal ECM, mesothelial ECM, thoracic cavity ECM, abdominal cavity ECM, pericardium ECM or dermal tissue ECM, and the sheet of ECM is infused with, coated with, or attached to an agent xenogeneic to a Urodele that is a growth factor, a cytokine, a chemokine, a protein, a carbohydrate, a sugar, a steroid, an antimicrobial agent, a synthetic polymer, an adhesive, or a drug.

15. The tissue graft of claim 14, wherein the agent is an anti-microbial agent.

16. The tissue graft of claim 14, wherein the agent is a growth factor.

17. The tissue graft of claim 14, wherein the sheet is at least two sheets of isolated Urodele decellularized ECM laminated to one another.

18. A method for making the tissue graft of claim 1, comprising extracellular matrix components derived from a Urodele, said method comprising:
  a. obtaining a tissue sample from a urodele, which tissue sample comprises extracellular matrix; and
  b. decellularizing said tissue sample to produce decellularized extracellular matrix by removing sufficient cellular components of the sample to reduce or eliminate antigenicity of the biomaterial making it suitable for use as a xenograft.

19. The method according to claim 18, wherein said decellularizing comprises subjecting said tissue sample to an alkaline treatment, and wherein said process further optionally comprises subjecting said sample to sterilization, and wherein the Urodele is an Axolotl.

20. A sterile medical implant comprising sterile, isolated, decellularized Urodele Extracellular Matrix (ECM) or a sterile Urodele fraction derived from the isolated, decellularized Urodele ECM produced by a process comprising:
  a. obtaining a tissue sample from a urodele, which tissue sample comprises extracellular matrix;
  b. decellularizing and sterilizing said tissue sample to produce decellularized extracellular matrix by removing sufficient cellular components of the sample to reduce or eliminate antigenicity of the biomaterial making it suitable for use as a xenograft; and sterilizing said tissue.

21. The sterile medical implant of claim 20, wherein the implant is a biocompatible sheet, mesh, gel, graft, tissue or device.

22. The sterile medical implant of claim 20, wherein the Urodele ECM includes basement membrane.

23. The sterile medical implant of claim 20, wherein the Urodele ECM is derived from Axolotl tissue.

24. The sterile medical implant of claim 20, wherein the Urodele ECM is infused with, coated with, or attached to an agent xenogenic to a Urodele that is a growth factor, a cytokine, a chemokine, a protein, a carbohydrate, a sugar, a steroid, an antimicrobial agent, a synthetic polymer, an adhesive, or a drug.

25. The sterile medical implant of claim 20, further comprising a human cell and wherein the Urodele ECM is infused with, coated with, or attached to the human cell.

26. The sterile medical implant of claim 20, wherein the Urodele extracellular matrix (ECM) or a sterile Urodele fraction derived from the isolated, decellularized Urodele ECM is a sheet.

27. The sterile medical implant of claim 20, wherein the Urodele ECM is in the form of Urodele ECM particles.

28. The sterile medical implant of claim 20, wherein the Urodele ECM is a reconstituted gel.

29. A method for making the sterile medical implant of claim 20, comprising sterile, isolated, decellularized Urodele Extracellular Matrix (ECM) or a sterile Urodele fraction derived from the isolated, decellularized Urodele ECM, said method comprising:
  a. obtaining a tissue sample from a urodele, which tissue sample comprises extracellular matrix;
  b. decellularizing and sterilizing said tissue sample, to produce the sterile decellularized extracellular matrix comprised within said sterile medical implant, by removing sufficient cellular components of the sample to reduce or eliminate antigenicity of the biomaterial, making it suitable for use as a xenograft; and sterilizing said tissue.

30. The method according to claim 29, wherein the implant is a biocompatible sheet, mesh, gel, graft, tissue, device, or is a material coated with, impregnated with, encapsulated with, or having attached thereto the isolated, decellularized Urodele ECM.

31. The method according to claim 29, wherein said decellularizing comprises subjecting said tissue sample to an alkaline treatment, wherein said process further comprises subjecting said sample to sterilization, wherein the Urodele is an Axolotl.

32. A material coated with, impregnated with, encapsulating, or having attached thereto isolated, decellularized Urodele ECM wherein said isolated, decellularized Urodele ECM is produced by a process comprising:
  a. obtaining a tissue sample from a urodele, which tissue sample comprises extracellular matrix;
  b. decellularizing said tissue sample to produce decellularized extracellular matrix by removing sufficient cellular components of the sample to reduce or eliminate antigenicity of the biomaterial making it suitable for use as a xenograft; and
  sterilizing said tissue.

33. The material of claim 32, wherein the Urodele ECM is Axolotl ECM.

34. A method for making the material coated with, impregnated with, encapsulating, or having attached thereto isolated, decellularized Urodele ECM of claim 32, wherein said isolated, decellularized Urodele ECM is produced by a process comprising:
  a. obtaining a tissue sample from a urodele, which tissue sample comprises extracellular matrix;
  b. decellularizing said tissue sample to produce decellularized extracellular matrix by removing sufficient cellular components of the sample to reduce or eliminate antigenicity of the biomaterial making it suitable for use as a xenograft; and sterilizing said tissue.

35. A device comprising a tissue graft according to claim 5 comprising at least two sheets of isolated Urodele decellularized ECM laminated to one another, wherein said extracellular matrix components are derived from a Urodele, said tissue graft derived by:
  a. obtaining a tissue sample from a urodele, which tissue sample comprises extracellular matrix; and
  b. decellularizing said tissue sample to produce decellularized extracellular matrix by removing sufficient cellular components of the sample to reduce or eliminate antigenicity of the biomaterial making it suitable for use as a xenograft.

36. The device of claim 35, wherein the Urodele ECM is Axolotl ECM.

* * * * *

UNITED STATES PATENT AND TRADEMARK OFFICE
CERTIFICATE OF CORRECTION

PATENT NO. : 10,617,790 B2
APPLICATION NO. : 14/759895
DATED : April 14, 2020
INVENTOR(S) : Early It is certified that error appears in the above-identified patent and that said Letters Patent is hereby corrected as shown below:

In the Specification

At Column 12, Line 17, "250 mm" should read --250 microns--.

At Column 19, Line 24, "post-cyromilling" should read --post-cryomilling--.

In the Claims

At Column 20, Line 52, in Claim 8, "The tissue graft of claim 6" should read --The tissue graft of claim 7--.

Signed and Sealed this
Twentieth Day of December, 2022

Katherine Kelly Vidal
*Director of the United States Patent and Trademark Office*